US009907702B2

(12) United States Patent
Kipke et al.

(10) Patent No.: US 9,907,702 B2
(45) Date of Patent: Mar. 6, 2018

(54) MONOMER-GRAFTED FIBERS AND USES THEREOF

(75) Inventors: Cary A. Kipke, Woodbury, MN (US); John J. Rogers, Saint Paul, MN (US); Michael R. Berrigan, Oakdale, MN (US); Clinton P. Waller, Jr., White Bear Lake, MN (US); Douglas E. Weiss, Overland Park, KS (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 407 days.

(21) Appl. No.: 14/237,205

(22) PCT Filed: Aug. 13, 2012

(86) PCT No.: PCT/US2012/050518
§ 371 (c)(1),
(2), (4) Date: Mar. 24, 2014

(87) PCT Pub. No.: WO2013/025579
PCT Pub. Date: Feb. 21, 2013

(65) Prior Publication Data
US 2014/0296765 A1  Oct. 2, 2014

Related U.S. Application Data

(60) Provisional application No. 61/524,417, filed on Aug. 17, 2011.

(51) Int. Cl.
| | | |
|---|---|---|
| *A61F 13/00* | (2006.01) |
| *D04H 1/425* | (2012.01) |
| *D04H 1/4382* | (2012.01) |
| *D06M 14/22* | (2006.01) |
| *D06M 10/00* | (2006.01) |
| *D06M 16/00* | (2006.01) |
| *A61L 15/44* | (2006.01) |
| *A61L 15/46* | (2006.01) |
| *A61L 15/60* | (2006.01) |
| *D06M 10/08* | (2006.01) |
| *D06M 14/24* | (2006.01) |
| *D06M 14/34* | (2006.01) |
| *A61F 13/15* | (2006.01) |

(52) U.S. Cl.
CPC .. *A61F 13/00008* (2013.01); *A61F 13/00012* (2013.01); *A61F 13/00042* (2013.01); *A61F 13/00063* (2013.01); *A61F 13/00068* (2013.01); *A61L 15/44* (2013.01); *A61L 15/46* (2013.01); *A61L 15/60* (2013.01); *D04H 1/425* (2013.01); *D04H 1/4382* (2013.01); *D06M 10/008* (2013.01); *D06M 10/08* (2013.01); *D06M 14/22* (2013.01); *D06M 14/24* (2013.01); *D06M 14/34* (2013.01); *D06M 16/00* (2013.01); *A61F 2013/00323* (2013.01); *A61F 2013/15463* (2013.01); *A61L 2420/02* (2013.01)

(58) Field of Classification Search
CPC .......... A61F 13/00004; A61F 13/00008; A61F 13/00012; A61F 13/00017; A61F 13/00042; A61F 2013/00323
USPC ........................ 602/41–43, 45; 424/443, 445
See application file for complete search history.

(56) References Cited

U.S. PATENT DOCUMENTS

| | | |
|---|---|---|
| 3,157,460 A | 11/1964 | Arthur |
| 3,682,802 A | 8/1972 | Sakurada |
| 3,779,881 A | 12/1973 | Sakurada |
| 3,814,676 A | 6/1974 | Williams |
| 4,157,418 A | 6/1979 | Heilmann |
| 4,212,649 A | 7/1980 | Sakurada |
| 4,277,242 A | 7/1981 | McLaren |
| 4,340,057 A | 7/1982 | Bloch |
| 4,810,567 A | 3/1989 | Calcaterra |
| 5,731,083 A | 3/1998 | Bahia et al. |
| 6,022,330 A | 2/2000 | Chen |
| 6,149,947 A | 11/2000 | Hon |
| 6,659,751 B1 | 12/2003 | Sugo |
| 6,838,589 B2 | 1/2005 | Liedtke |
| 6,844,066 B2 | 1/2005 | Hamed |
| 7,014,870 B1 | 3/2006 | Hon |
| 7,652,189 B2 | 1/2010 | Bray |
| 2003/0135039 A1* | 7/2003 | Makino ............... C12N 15/1006 536/25.4 |
| 2003/0180346 A1 | 9/2003 | Woods |
| 2006/0105017 A1 | 5/2006 | Walboomers |
| 2008/0230471 A1 | 9/2008 | Tamada |
| 2009/0092645 A1 | 4/2009 | Wu |

(Continued)

FOREIGN PATENT DOCUMENTS

| | | |
|---|---|---|
| GB | 895478 | 5/1962 |
| JP | H07(1995)-179630 | 7/1995 |

(Continued)

OTHER PUBLICATIONS

Childs, "Nanofiltration using pore-filled membranes: effect of polyelectrolyte composition on performance", Separation and Purification Technology, 2001, vol. 22-23, pp. 507-517.

Davies, "The Separation of Airborne Dust and Particles", Institution of Mechanical Engineers, Proceedings (B), 1952, vol. IB, No. 1-12, pp. 185-198.

Mika, "A new class of polyelectrolyte-filled microfiltration membranes with environmentally controlled porosity", Journal of Membrane Science, 1995, vol. 108, pp. 37-56.

Mika, "Poly (4-vinylpyridine)-filled microfiltration membranes: physicochemical properties and morphology", Journal of Membrane Science, 1997, vol. 136, pp. 221-232.

(Continued)

*Primary Examiner* — Keri J Nelson
(74) *Attorney, Agent, or Firm* — 3M Innovative Properties Company; Lynn R. Hunsberger

(57) ABSTRACT

Wound dressing articles comprising a nonwoven web comprising a plurality of fibers having grafted pendant hydrophilic groups, methods that use high energy irradiation for making a plurality of fibers having grafted pendant hydrophilic groups, useful for making wound dressing articles.

13 Claims, No Drawings

(56) References Cited

U.S. PATENT DOCUMENTS

| | | |
|---|---|---|
| 2009/0176908 A1 | 7/2009 | Busam |
| 2010/0035492 A1 | 2/2010 | Colin |
| 2010/0155323 A1 | 6/2010 | Weiss |
| 2010/0166823 A1* | 7/2010 | Li .................. A61K 9/0014 424/423 |

FOREIGN PATENT DOCUMENTS

| | | |
|---|---|---|
| WO | WO 03/053483 | 7/2003 |
| WO | WO 2007/085884 | 8/2007 |
| WO | WO 2010-033794 | 3/2010 |
| WO | WO 2010-151447 | 12/2010 |

OTHER PUBLICATIONS

Mika, "Porous, polyelectrolyte-filled membranes: Effect of cross-linking on flux and separation", Journal of Membrane Science, 1997, vol. 135, pp. 81-92.

Nechifor, "The Influence of Gamma Radiations on Physico-Chemical Properties of Some Polymer Membranes", Romania Journal of. Physics, 2009, vol. 54, No, 3-4, pp. 349-359.

Slater, "Tencel® A Versatile, High Performance Fibre for Nonwovens", Lenzinger Berichte, 2003, vol. 82, pp. 37-42.

International Search Report for PCT International Application No. PCT/US2012/050518 dated May 2, 2013, 4 pages.

\* cited by examiner

MONOMER-GRAFTED FIBERS AND USES THEREOF

CROSS REFERENCE TO RELATED APPLICATIONS

This application is a national stage filing under 35 U.S.C. 371 of PCT/US2012/0505018, filed Aug. 13, 2012, which claims priority to U.S. Provisional Application No. 61/524,417 filed Aug. 17, 2011, the disclosures of which are incorporated by reference in their entirety herein.

BACKGROUND

Carboxymethylcellulose fiber for use in absorbent personal products is known, derived from solvent-spun cellulose fibers, for example by reaction with a strong alkali and a monochloroacetate reagent. See, for example, U.S. Pat. No. 5,731,083 (Bahia et al.).

SUMMARY

The present disclosure relates to a wound dressing with hydrophilic monomer-grafted fibers. In one aspect, the present disclosure describes a wound dressing comprises a nonwoven web comprising a plurality of fibers irradiation-grafted with individual polymer chains that extend from the surface of the fibers; wherein fibers in the plurality of fibers comprise fiber repeat units; wherein the individual polymer chains comprise hydrophilic monomer units each comprising at least one hydrophilic group; and wherein the plurality of fibers in the nonwoven web have a ratio of hydrophilic groups to fiber repeat units in a range of from 0.25 to 5.0. In some embodiments, the individual polymer chains comprise acrylic acid monomer units. In some embodiments, the individual polymer chains comprise acrylic acid monomer units and polyethylene glycol monomer units.

In another aspect, the present disclosure describes to a method of making a plurality of irradiated fibers having grafted pendant hydrophilic groups, the method comprising providing a plurality of fibers; irradiating the plurality of fibers with a high energy irradiation to generate an irradiated plurality of fibers; providing an aqueous solution comprising hydrophilic monomers; contacting the irradiated plurality of fibers with the aqueous solution such that the irradiated plurality of fibers is grafted with the hydrophilic monomers to provide a plurality of irradiated fibers having individual polymer chains extending from the surface thereof, wherein the individual polymer chains comprise hydrophilic groups; and removing residual hydrophilic monomers from the plurality of irradiated fibers. In some embodiments, the hydrophilic monomers comprise acrylic acid. In some embodiments, the hydrophilic monomers comprise acrylic acid and a polyethylene glycol.

In another aspect, the present disclosure describes a method of making a hydrophilic nonwoven article, comprising: making a plurality of irradiated fibers having grafted pendant hydrophilic groups according to the above method of making a plurality of irradiated fibers having grafted pendant hydrophilic groups of the present disclosure; and forming a nonwoven article from the plurality of irradiated fibers having grafted pendant hydrophilic groups.

In another aspect, the present disclosure describes a method of making a hydrophilic nonwoven article, comprising: making a first plurality of irradiated fibers having grafted pendant hydrophilic groups according to the above method of making a plurality of irradiated fibers having grafted pendant hydrophilic groups of the present disclosure; providing a second plurality of fibers not treated according to the above method of making a plurality of irradiated fibers having grafted pendant hydrophilic groups of the present disclosure; and forming a nonwoven article from the first plurality of fibers and the second plurality of fibers.

In another aspect, the present disclosure describes a method of making a hydrophilic nonwoven article, comprising: making a first plurality of irradiated fibers having grafted pendant hydrophilic groups according to the above method of making a plurality of irradiated fibers having grafted pendant hydrophilic groups of the present disclosure; making a second plurality of fibers having grafted pendant hydrophilic groups according to the above method of making a plurality of irradiated fibers having grafted pendant hydrophilic groups of the present disclosure; and forming a nonwoven article from the first plurality of fibers and the second plurality of fibers; wherein the first and second pluralities of fibers differ from each other in composition.

In another aspect, the present disclosure describes a method of making a hydrophilic nonwoven article, comprising: making a plurality of hydrophilic fibers having grafted pendant hydrophilic groups according to the method of disclosure; and forming a nonwoven article from the plurality of hydrophilic fibers.

In another aspect, the present disclosure describes a method of treating a wound, comprising: providing a hydrophilic nonwoven article according to the method of the present disclosure; and contacting the hydrophilic nonwoven article onto a wound.

"Adjacent to a wound" refers to being in direct contact with a wound, optionally including at least one intervening layer of material between a wound and an article of the present disclosure said to contact a wound.

"Nonwoven" refers to a textile structure produced by bonding or interlocking of fibers, or both, accomplished by mechanical, chemical, thermal, or solvent means and combinations in accordance with ASTM D123-09e1.

Wound dressings of the present disclosure are useful for treating wounds that have an exudate, especially for absorption of fluid from highly exudating wounds.

DETAILED DESCRIPTION

A wound dressing article of the present disclosure has a nonwoven web of super-absorbent fibers. While many types of super-absorbent fibers are known, the super-absorbent fibers according to the present disclosure have pendant hydrophilic groups grafted onto fibers, using high energy radiation to graft hydrophilic monomers onto any of various types of fiber, including natural fiber (e.g., cotton fiber, wool fiber) and/or synthetic fiber (e.g., rayon, nylon, regenerated cellulose fiber).

By using high energy irradiation (e.g., e-beam irradiation, gamma irradiation) to initiate a grafting reaction, the need for various commonly used initiator reagents can be obviated, and the resulting grafted fiber (and ultimately, the wound dressing) is free of those initiator reagents used in, for example, grafting reactions initiated with ultraviolet light or thermal processes. Further, a plurality of fibers can be irradiated with high energy irradiation and reacted with hydrophilic monomers, and residual hydrophilic monomers, if present, can be removed with a washing process, providing a plurality of irradiated fibers having grafted pendant hydrophilic groups and a high level of purity, which is generally desirable in the production of wound dressing articles. It has been observed that the use of ionizing radiation in the methods of the present disclosure can minimize solution polymerization of the hydrophilic monomers, obviating the need to remove those hydrophilic polymers by an exhaustive washing process.

A particularly useful synthetic fiber for use in grafting methods of the present disclosure is that regenerated cellulose fiber referred to as "Lyocell", for example, that Lyocell fiber available from Lenzing AG (Mobile, Ala.) under the trade designation "TENCEL". For additional description of TENCEL, including the useful HS260 grade, see, e.g., Slater et al., *Lenzinger Berichte*, 82 (2003), pp. 37-42. Various sizes of Lyocell fibers can be used (e.g., 1.7 decitex×38 mm, or 1.7 decitex×51 mm, or 3.3 decitex×60 mm to 90 mm, or 1.3 decitex×38 mm, or other suitable fiber dimensions).

Fibers comprise "fiber repeat units" (i.e., monomers). For example, cellulose has repeat units of glucose molecules, and nylon has various repeat units of amide-linked molecules.

The pendant hydrophilic groups typically are part of a grafted polymer comprising "anionic" monomer units, "neutral hydrophilic" monomer units, or combinations of anionic and neutral hydrophilic monomer units grafted to the surface(s) of plurality of fibers.

Hydrophilic monomers for use in grafting methods of the present disclosure include those hydrophilic monomers having at least one unsaturated double bond. The hydrophilic monomers can include "anionic" (i.e., negatively charged) monomers, "cationic" (i.e., positively charged) monomers, "neutral" (i.e., neither negatively nor positively charged) hydrophilic monomers, or any combination of these.

The negatively charged anionic monomer has at least one ethylenically unsaturated group capable of undergoing free radical polymerization, and an additional anionic functional group. In some embodiments, the ethylenically unsaturated group is a (meth)acryloyl group or a vinyl group. The anionic monomer can be a weak acid, a strong acid, a salt of a weak acid, a salt of a strong acid, or combination thereof. If the anionic monomer used to prepare a hydrophilic fiber includes a salt of a weak acid or a salt of a strong acid, the counter ions of these salts can be, but are not limited to, alkali metals, alkaline earth metals, ammonium ions, or tetraalkylammonium ions.

Suitable anionic monomers include acrylic acid and methacrylic acid; sulfonic acids such as vinylsulfonic acid and 4-styrenesulfonic acid; (meth)acrylamidophosphonic acids such as (meth)acrylamidoalkylphosphonic acids (e.g., 2-acrylamidoethylphosphonic acid and 3-methacrylamidopropylphosphonic acid); and carboxyalkyl(meth)acrylates such as 2-carboxyethylacrylate, 2-carboxyethylmethacrylate, 3-carboxypropylacrylate, and 3-carboxypropylmethacrylate. Still other suitable acidic monomers include (meth) acryloylamino acids (e.g., N-acryloylglycine, N-acryloylaspartic acid, N-acryloyl-β-alanine, 2-acrylamidoglycolic acid, 3-acrylamido-3-methylbutyric acid, and those described in U.S. Pat. No. 4,157,418 (Heilmann), incorporated herein by reference). Salts of any of these acidic monomers can also be used.

Other suitable anionic monomers may have the general formula (I):

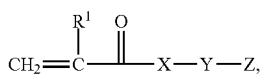

where
$R^1$ is H or $CH_3$;
X is —O— or —$NR^1$—,
Y is a straight or branched chain alkylene, generally from 1 to 10 carbon atoms; and
Z is an anionic group, which may be selected from sulphonic acids groups, phosphonic acid groups, and carboxylic acid groups, and salts thereof.

Some exemplary anionic monomers include (meth)acrylamidosulfonic acids of Formula (II) or salts thereof:

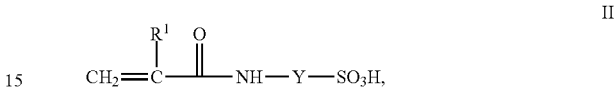

where
$R^1$ is H or $CH_3$, and Y is a straight or branched alkylene having 1 to 10 carbon atoms. Exemplary ionic monomers according to Formula (II) include, but are not limited to, N-acrylamidomethanesulfonic acid, 2-acrylamidoethanesulfonic acid, 2-acrylamido-2-methylpropanesulfonic acid, and 2-methacrylamido-2-methylpropanesulfonic acid. Salts of these acidic monomers can also be used, examples being (3-sulfopropyl)-methacrylic acid potassium salt and 2-(methacryloyloxy)ethylsulfonic acid sodium salt.

The grafted polymer optionally contains monofunctional ethylenically-unsaturated grafting monomer units having a poly(alkylene oxide) group. These monomers copolymerize with the grafting anionic monomers to form a grafted copolymer chain on the surface of the substrate. When present, these monomers are used in amounts of 2 to 25 wt. %, and more desirably 4 to 20 wt. %, relative to the total monomer weight.

The monomer units having a poly(alkylene oxide) group is of the formula:

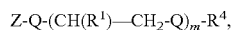

wherein Z is a polymerizable ethylenically unsaturated moiety, $R^1$ is a H or $CH_3$, $R^4$ is a H, a $C_1$ to $C_4$ alkyl group, aryl group, or combination thereof and m is from 2 to 100, preferably 5 to 20, and Q is a divalent linking group selected from —O—, —$NR^1$—, —$CO_2$— and —$CONR^1$. In one embodiment, the poly(alkylene oxide) group is a poly(ethylene oxide) (co)polymer.

In another embodiment, the pendent poly(alkylene oxide) group is a poly(ethylene oxide-co-propylene oxide) copolymer. Such copolymers may be block copolymers, random copolymers, or gradient copolymers.

Useful ethylenically unsaturated moiety, Z, of the monomer may include:

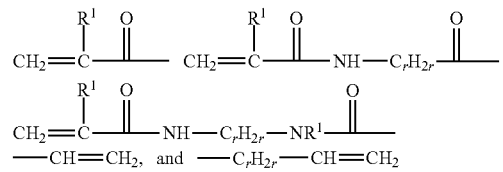

wherein $R^1$ is H or Me and r=1-10.

The monomer having a poly(alkylene oxide) group can be prepared, for example, by reacting mono- or di-functional alkylene oxide (co)polymers (which are typically commercially available) with reactive ethylenically unsaturated compounds (e.g., acrylates). The functional groups terminating the poly(alkylene oxide) may include hydroxy groups, amine groups and carboxyl groups. A variety of reactive ethylenically unsaturated compounds such as acrylate derivatives can be used including, but not limited to, (meth)acrylic acid, (meth)acryloyl chloride, (meth)acrylic anhydride, and 2-isocyanatoethyl(meth)acrylate. Preferably, the monomer is prepared by reacting the mono- or di-functional alkylene oxide (co)polymer with (meth)acrylic anhydride. Typically, if a stoichiometric amount of the ethylenically unsaturated reactant is combined with the monofunctional alkylene oxide (co)polymer (such as a monohydroxy terminated alkylene oxide (co)polymer), 100% conversion to the monosubstituted product is obtained.

Examples of suitable monofunctional poly(alkylene oxide) monomers include poly(ethylene oxide) (meth)acrylate, poly(propylene oxide) (meth)acrylate, poly(ethylene oxide-propylene oxide) (meth)acrylate, and combinations thereof. Such monomers preferably include one nonreactive end group such as ($C_1$-$C_4$)alkoxy, aryloxy (e.g., phenoxy), and ($C_1$-$C_4$)alkaryloxy. These groups can be linear or branched. These monomers can be of a wide range of molecular weights and are commercially available from sources such as Sartomer Company, Exton, Pa. (including that methoxy polyethylene obtained under the trade designation "SR550"); Shinnakamura Chemical Co., Ltd., Tokyo, Japan; Aldrich, Milwaukee, Wis.; and Osaka Organic Chemical Ind., Ltd., Osaka, Japan.

Additional examples of suitable neutral hydrophilic monomers include 2-hydroxyethyl(meth)acrylate (HEMA), 2-hydroxypropyl(meth)acrylate, 3-hydroxypropyl(meth)acrylate, 2,3-dihydroxypropyl(meth)acrylate, 4-hydroxybutyl(meth)acrylate, N-vinyl caprolactam, N-vinyl acetamide, N-vinyl pyrrolidone, acrylonitrile, tetrahydrofurfuryl acrylate, acrylamide, mono- or di-N-alkyl substituted acrylamide, glycerol methacrylate, and combinations thereof. Among these additional examples of suitable neutral hydrophilic monomers, particularly suitable examples include 2-hydroxyethyl(meth)acrylate (HEMA), N-vinyl pyrrolidone, N-vinyl acetamide, methylacrylamide, and mixtures thereof.

In some embodiments neutral hydrophilic monomers can include hydrophilic groups that are any of hydroxyalkyl, methoxyalkyl, polyethyleneglycol, methoxy polyethyleneglycol, or any combination of these.

As the polymer is preferably uncrosslinked, the imbibing solution containing the monomer mixture preferably contains no polyethylenically unsaturated monomers (i.e., no crosslinkers).

In some typical embodiments, the total grafted hydrophilic monomer content may be from 0.75 to 2 times the weight of the plurality of irradiated fibers having grafted pendant hydrophilic groups. It is desirable to avoid having polymer chains forming bridges to link separate fibers, as this may reduce the availability of hydrophilic groups to absorb wound fluid. One way to minimize fiber-fiber bridging by the grafted polymer is to lower the monomer concentration for a given fiber size. Another way to avoid bridging includes lowering the dose of high energy irradiation, which, without being bound by theory, increases the space between free radicals generated on the surface of the irradiated fibers.

The grafted hydrophilic monomer units extend from the surface of the fibers as a individual (i.e., uncrosslinked) polymer chain. In this grafting method, a repeat unit of the fiber is grafted with a first hydrophilic monomer unit, which reacts with a second hydrophilic monomer unit, to grow an individual polymer chain that extends from the surface of the fiber. The attachment point of the first hydrophilic monomer unit will be random depending on where the high energy irradiation generates free radicals (typically, from either a carbon atom or an oxygen atom).

The polymer chains are not cross-linked to any appreciable extent. The intent of the current method is to form individual, non-crosslinked) polymer chains extending from the surface of the fibers. In some embodiments it may be desirable to add a water miscible organic solvent to the grafting imbibing solution to enhance the molecular weight of the grafted individual polymer chains and reduce bridging of the polymer chains.

The presently described method can be distinguished over methods that from a bond between a hydroxyl group on a fiber repeat unit and a hydrophilic group, for example, as in the case of carboxymethylation of cellulose with chloroacetic acid.

It has been observed that the inclusion of PEG co-monomers can result in less brittle fibers, and fibers with softer "feel", as compared with, for example, fibers grafted with 100% acrylic acid. It has also been observed that the grafted fibers of the present disclosure can re-open for web-making more easily in the presence of a lubricant, and that a PEG monomer provides some lubricant properties. Alternatively, a PEG additive (e.g., PEG 400) can be added to the grafted fibers. Other lubricants for enhancing the fiber processing are known to those having skill in the art.

The irradiated fibers having grafted pendant hydrophilic groups have an increased ability to absorb water relative to the corresponding non-grafted fibers. In some embodiments, the level of water absorption, as a Water Absorbency Ratio (see Example section) can increase by more than 10 times. In some embodiments, the level of water absorption, as a Water Absorption Ratio, can increase by up to 15 times, by up to 20 times, by up to 25 times, or even by up to 30 times, relative to the corresponding non-grafted fibers.

In some embodiments, useful fiber lengths can include from 51 mm-90 mm have been used. Shorter fiber lengths may also be useful, although processing techniques (e.g., needle tacking) may benefit from using the longer fibers.

It has been observed that in some embodiments, grafting efficiency can depend on fiber surface area. Without being bound by theory, it is thought that as the fiber surface area increases, water absorbency will increase, and as the fiber surface area decreases the water absorbency will decrease.

In the present disclosure, typical processes of preparing the plurality of irradiated fibers having grafted pendant hydrophilic groups comprise the steps of providing a plurality of fibers ("substrate"), irradiating the plurality of fibers with high energy radiation (typically in an inert atmosphere), and subsequently contacting (typically by imbibing) the exposed substrate with a solution comprising anionic monomers (and optionally other monomers, as described) to graft polymerize said monomers to the surface(s) of the plurality of fibers.

In the first step the substrate is exposed to ionizing radiation, such as e-beam irradiation, in an inert atmosphere. Generally, the substrate is placed in a container purged of oxygen. Typically, the container comprises an inert atmosphere such as nitrogen, carbon dioxide, helium, argon, etc., with a minimal amount of oxygen (less than 100 ppm), which is known to inhibit free-radical polymerization. Suitable containers can include a sealed polymeric bag, for example. In the case of using gamma irradiation, a metal container (e.g., aluminum) may be used.

The irradiation step comprises exposing the substrate to ionizing irradiation, preferably with ionizing e-beam or gamma radiation to prepare free radical reaction sites on such surfaces upon which the monomers are subsequently grafted. "Ionizing irradiation" means radiation of a sufficient dosage and energy to cause the formation of free radical reaction sites on the surface(s) of the base substrate. Ionizing radiation may include gamma, electron-beam, x-ray and other forms of electromagnetic radiation. In some instances, corona radiation may be used. The radiation is sufficiently high energy, that when absorbed by the surfaces of the base substrate, sufficient energy is transferred to the substrate to result in the cleavage of chemical bonds in the substrate and the resultant formation of free radical sites on the substrate.

High energy radiation dosages are measured in units of kilogray (kGy). Doses can be administered in a single dose of the desired level or in multiple doses which accumulate to the desired level. Generally, good results may be achieved in the range of 40-100 kGy. The dose can be delivered all at once such as from an E-beam source or accumulated from a slow dose rate over several hours such as dosage delivered from a gamma source.

Electron beam is one preferred method of grafting due to the ready-availability of commercial sources. Electron beam generators are commercially available from a variety of sources, including the ESI "ELECTROCURE" EB SYSTEM from Energy Sciences, Inc. (Wilmington, Mass.), the BROADBEAM EB PROCESSOR from PCT Engineered Systems, LLC (Davenport, Iowa), and those systems available from ADVANCED ELECTRON BEAMS (AEB, Wilmington, Mass.). For any given piece of equipment and irradiation sample location, the dosage delivered can be measured in accordance with ISO/ASTM 51818 entitled "Standard practice for dosimetry in an electron beam facility for radiation processing at energies between 80 and 300 keV". By altering extractor grid voltage, beam diameter and/or distance to the source, various dose rates can be obtained.

In the irradiation step the substrate is exposed to a sufficient quantity of ionizing radiation, so as to form free radicals on the surface(s) of the substrate. The chamber may contain at least one device capable of providing a sufficient dose of radiation. A single device is capable of providing a sufficient dose of radiation, although two or more devices, and/or multiple passes through a single device, may be used especially for relatively thick substrates. The environment containing the substrate comprises an inert atmosphere such as nitrogen, carbon dioxide, helium, argon, etc., with a minimal amount of oxygen, which is known to inhibit free-radical polymerization.

Dose is the total amount of energy absorbed per mass unit. Dose is commonly expressed in units of kiloGray (kGy), or alternatively, megarad (Mrad; 10 kGy=1 Mrad). A gray is defined as the amount of radiation required to supply 1 joule of energy per kilogram of mass. The total dose received by the substrate depends on a number of parameters including source activity, residence time (i.e., the total time the sample is irradiated), the distance from the source, and attenuation by the intervening cross-section of materials between the source and sample. Dose is typically regulated by controlling residence time, distance to the source, or both. For electron beam irradiation, dose is principally determined by beam current and web speed (and voltage, if applicable).

Generally, it was found that doses in the range of about 50-70 kGy (i.e., 5-7 MRad) were suitable for generating the grafted individual polymer chains extending from the surface of the plurality of fibers. Total dose requirement for any given composition will vary as a function of desired grafting objectives, monomer selected, substrate used and the dose rate. Thus, a dose rate can be selected based on desired properties for a specified composition. The dose rate is typically in the range of 0.0005 kGy/sec (gamma) to 200 kGy/sec (E-beam).

Other sources of irradiation may be used with equal grafting performance; a desirable source of ionizing radiation comprises an electron beam source because the electron beam can produce high and fast dose delivery rates. Electron beams (e-beams) are generally produced by applying high voltage to tungsten wire filaments retained between a repeller plate and an extractor grid within a vacuum chamber maintained at about $10^{-6}$ Torr. The filaments are heated at high current to produce electrons. The electrons are guided and accelerated by the repeller plate and extractor grid towards a thin window of metal foil. The accelerated electrons, traveling at speeds in excess of $10^7$ meters/second (m/sec) and possessing about 100 to 300 kilo-electron volts (keV), pass out of the vacuum chamber through the foil window and penetrate whatever material is positioned immediately beyond the foil window.

The quantity of electrons generated is directly related to the current. As extractor grid voltage is increased, the acceleration (or speed) of electrons drawn from the tungsten wire filaments increases. E-beam processing can be extremely precise when under computer control, such that an exact dose and dose rate of electrons can be directed against the substrate.

The temperature within the chamber is desirably maintained at an ambient temperature by conventional means. Without intending to be limited to any particular mechanism, it is believed that the exposure of the substrate to an electron beam results in free radical sites on the substrate surface which can then subsequently react with the grafting monomers in the imbibing step.

The total dose received by the substrate primarily affects the number of radical sites formed on the surface thereof and subsequently the extent to which the grafting monomers are grafted onto the substrate. Dose is dependent upon a number of processing parameters, including voltage, web- or line-speed and beam current. Dose can be conveniently regulated by controlling line speed (i.e., the speed with which the substrate passes under the irradiation device), and the current supplied to the extractor grid. A target dose (e.g., <10 kGy) can be conveniently calculated by multiplying an experimentally measured coefficient (a machine constant) by the beam current and dividing by the web speed to determine the exposure. The machine constant varies as a function of beam voltage.

While the controlled amount of electron beam radiation exposure is dependent upon the residence time, the substrate is subjected to a controlled amount of dosage ranging from a minimum dosage of about 1 kilogray (kGy) to a practical maximum dosage of less than about 200 kGy, depending on the particular polymer. Generally, suitable gamma ray sources emit gamma rays having energies of 400 keV or greater. Typically, suitable gamma ray sources emit gamma rays having energies in the range of 500 keV to 5 MeV. Examples of suitable gamma ray sources include cobalt-60 isotope (which emits photons with energies of approximately 1.17 and 1.33 MeV in nearly equal proportions) and cesium-137 isotope (which emits photons with energies of approximately 0.662 MeV). The distance from the source can be fixed or made variable by changing the position of the target or the source. The flux of gamma rays emitted from the source generally decays with the square of the distance from the source and duration of time as governed by the half-life of the isotope.

In the instant method, the irradiated substrate, having free radical sites on the surface of the substrate, are imbibed with the monomer solution subsequent to and not concurrent with, the irradiation step. The free radical sites generated on the surface of the substrate have average lifetimes ranging from several minutes to several hours and progressively decay to a low concentration within about ten hours at room temperature. Lower temperatures, such as dry ice temperatures, promote longer radical lifetimes. Alternatively, humidification and nitrous oxide can increase the rate of substrate radical formation via generation of hydroxyl radicals. The effective binding absorption capacity of the grafted nonwoven from the graft polymerization process is little changed after a reaction time of about 12 hours, when kept under inert conditions. It has been observed that a reaction time of about 2 hours can be sufficient for achieving a desired level of graft polymerization.

Generally, the irradiated substrate is imbibed with the monomer solution immediately after the irradiation step. Generally when using E-beam the irradiated substrate is imbibed within an hour, preferably within ten minutes. Generally, when using gamma irradiation, the irradiated substrate is typically brought into contact with the aqueous solution of hydrophilic monomers within minutes after irradiation since irradiation residence time will be long. It has been observed that keeping the irradiated substrate at a reduced temperature (e.g., dry ice cooling) can extend the useful period of time between irradiation of the plurality of fibers and contacting the aqueous solution of hydrophilic monomers. Because of the typically long residence time in a gamma facility (hours) and at elevated temperature, it is preferred to pack the materials to be irradiated in dry ice or another heat-sink material to prevent free radicals being formed from degrading during the long exposure time.

The imbibing solution remains in contact with the substrate (after irradiation of the substrate) for a time sufficient for the radical sites to initiate polymerization with the grafting monomers. When imbibed with a solution of monomers, grafting reactions are mostly completed after 12 hours exposure; generally resulting in about 50+ percent conversion of monomers to grafted polymer. As a result, the substrate comprises grafted polymers and/or copolymers attached to the interstitial and outer surfaces of the substrate.

As discussed above, the imbibing solution may comprise one or more grafting monomers suitable for grafting onto surfaces of the substrate. Any of the exemplary grafting monomers described above can be included in the imbibing solution.

The concentration of each grafting monomer in the imbibing solution may vary depending on a number of factors including, but not limited to, the grafting monomer or monomers in the imbibing solution, the extent of grafting desired, the reactivity of the grafting monomer(s), and the solvent used. Typically, the total concentration of the monomers in the imbibing solution ranges from about 1 wt. % to about 100 wt. %, desirably, from about 2 wt. % to about 25 wt. %, and more desirably from about 4 wt. % to about 20 wt. % based on a total weight of the imbibing solution.

Once the substrate has been imbibed for a desired period of time, the substrate bearing grafted polymer groups is typically washed to remove residual monomer. In the washing step, the functionalized fiber substrate is washed or rinsed one or more times to remove any unreacted monomers, solvent or other reaction by-products. Typically, the functionalized substrate is washed or rinsed several times (e.g., three times) using a water rinse. In some embodiments, it may be useful to wash the grafted fibers with either an acid or a base (e.g., a sodium hydroxide solution). In each rinse step, the functionalized substrate may pass through a rinse bath or a rinse spray.

When using water soluble monomers, the grafted fibers are typically washed using water. If one of the grafted monomers is acidic and/or basic, it is advantageous to conduct the washing process prior to converting the acid or base to a salt form. The removal of impurities from grafted fiber reactions is best conducted prior to introducing superabsorbent properties to the fibers as shown in examples that monitor the Total Organic Carbon level in a wash solution prepared for that test method (see Example section).

In an optional drying step, the functionalized substrate is dried to remove any rinse solution. Typically, the functionalized substrate is dried in oven having a relatively low oven temperature for a desired period of time (referred to herein as "oven dwell time"). Oven temperatures typically range from about 40° C. to about 120° C., while oven dwell times typically range from about 1 minute to about 30 minutes. Any conventional oven may be used in the optional drying step. It should also be noted that in other embodiments the drying step can proceed before the rinsing step to eliminate volatile components before extraction of non-grafted residue.

In some embodiments, it is desirable to form a salt of hydrophilic groups on the grafted fibers, where the group is "reactable" with an acid or a base to form a salt. For example, when the grafted fibers include carboxylic acid or sulfonic acid groups as the hydrophilic groups, the grafted fibers can be treated with a sodium hydroxide solution to convert the acid groups to sodium salts. In some embodiments, it may be desirable to form a variety of other suitable metal salts of the reactable groups on the grafted fibers. For example, the fibers having the sodium salt described as above can be soaked in an aqueous solution of salts to effect an exchange of the metal ion. In some embodiments, suitable metal ions can include any of sodium ions, potassium ions, rubidium ions, zinc ions, calcium ions, or any combinations of these ions. Various combinations of these metal ions can have a beneficial effect towards treatment of wounds, as described, for example, in U.S. Pat. Nos. 6,149,947 and 7,014,870, the disclosure of each of which is incorporated herein by reference in its entirety.

Fibers of the present disclosure having grafted pendant hydrophilic groups can be formed into a nonwoven web, using conventional techniques (e.g., use of Rando equipment, carding, random carding, entangling). The nonwoven web can be further processed by techniques including, for example, cross-lapping and needle tacking. In some embodiments, it may be desirable to add a binder fiber or other types of fibers in forming the nonwoven web. Various combinations of these web-forming techniques know to those having skill in the art can be used in the formation of the wound dressing article of the present disclosure.

Typically, for wound dressings of the present disclosure, the nonwoven web has a specific density of no more than 0.1 gram per cubic centimeter (in some embodiments, no more than 0.08 gram per cubic centimeter, or even no more than 0.05 gram per cubic centimeter). In some embodiments, the specific density of the nonwoven web can be no more than 0.2 grams per cubic centimeter. The specific density of a nonwoven web is then determined by weighing a sample of a given thickness and also determining the sample volume (area×thickness). The thickness of nonwoven web specimens can be determined according to the method set forth in Davies, C. N., "The Separation of Airborne Dust and Particles", Institution of Mechanical Engineers, London, Proceeding 1B, 1952. Typically, a 10 cm×10 cm sample of the grafted nonwoven web is useful for making the specific density measurement. Using a nonwoven web having grafted cellulose fibers as an example, the specific density can be calculated as {total mass of the sample divided by [(mass fraction of cellulose times the cellulose density) plus (mass fraction of grafted polymer times density of the grafted polymer)]} divided by the sample volume.

It will be appreciated that various combinations of hydrophilic monomers can be selected to achieve desired combinations of water absorption level, texture, strength, or other properties in the wound dressing. It will also be appreciated that the wound dressing may include more than one nonwoven web (e.g., more than one layer of nonwoven webs can be included in the wound dressing), so that many configurations of wound dressings can be produced.

While the present disclosure primarily describes high energy radiation grafting of a plurality of fibers, it will be appreciated that the plurality of fibers can be in the form of a thread, a tow, fiber pulp, or a rope.

In some embodiments, the wound dressing of the present disclosure can include one or more medicaments. For example, an antimicrobial agent, or an antibiotic, or an anesthetic agent, or an anti-inflammatory agent, or a skin protective agent, or a substance intended to negate malodors, can be incorporated. Suitable antimicrobial agents can include, for example, any of silver, silver-containing compounds, povidone iodine, quaternized amines, polyhexamethylbiguanine (PHMB) and formulations which release hydrogen peroxide.

The incorporation of a medicament can be achieved in a variety of ways. For example, silver or other metal ions can be chemically bound by ion-exchange reactions. Other medicaments might be added during the last stage of, or in an additional stage following, the radiation grafting process by contacting a solution of the medicament with the fibers which are then dried, leaving a deposit of the medicament on the surface of the fibers.

In some embodiments, wound dressing articles of the present disclosure can be packed into a wound, as the nonwoven web, without requiring any backing material. Optionally, the nonwoven web can be held in place with a tape, bandage, a porous containment enclosure (e.g. a mesh) to provide access to wound fluid, but not allow fibers to migrate outside the mesh.

Embodiments (provided as a list of "Items:):
Item 1. A wound dressing comprising:
   a nonwoven web comprising a plurality of fibers irradiation-grafted with individual polymer chains that extend from the surface of the fibers;
   wherein fibers in the plurality of fibers comprise fiber repeat units;
   wherein the individual polymer chains comprise hydrophilic monomer units each comprising at least one hydrophilic group; and
   wherein the plurality of fibers in the nonwoven web have a ratio of hydrophilic groups to fiber repeat units in a range of from 0.25 to 5.0.
Item 2. The wound dressing of item 1, wherein the nonwoven web has a specific density of no more than 0.1 gram per cubic centimeter.
Item 3. The wound dressing of item 1, wherein the plurality of fibers comprise cellulose.

Item 4. The wound dressing of any preceding item, wherein the individual polymer chains comprise acrylic acid monomer units.
Item 5. The wound dressing of item 4, wherein the individual polymer chains further comprise polyethylene glycol monomer units.
Item 6. The wound dressing of any preceding item, wherein the hydrophilic groups comprise any of carboxylic acid, hydroxyalkyl, methoxyalkyl, polyethyleneglycol, methoxy polyethyleneglycol, or combinations thereof.
Item 7. The wound dressing of any preceding item, wherein the hydrophilic groups comprise carboxylic acid groups or a salt thereof, or a combination of carboxylic acid groups and salts thereof.
Item 8. The wound dressing of item 7, wherein the salt comprises metal ions, wherein the metal ions comprise any of sodium ions, potassium ions, rubidium ions, zinc ions, calcium ions, or combinations thereof.
Item 9. The wound dressing of any preceding item, wherein the plurality of fibers have a Water Absorbency Ratio of at least 15 according to the Water Absorbency test method.
Item 10. The wound dressing of any preceding item, wherein the plurality fibers have a Water Absorbency Ratio of at least 20 according to the Water Absorbency test method.
Item 11. The wound dressing of any preceding item, further comprising at least one of an antibacterial agent, an anti-inflammatory agent, an anesthetic agent, an anti-odor agent, or combinations thereof.
Item 12. The wound dressing of any preceding item, wherein at least a portion of the nonwoven web is adjacent to a wound.
Item 13. The wound dressing of any preceding item, wherein at least a portion of the nonwoven web absorbs wound fluid.
Item 14. A method of making a plurality of irradiation-grafted fibers, the method comprising:
   providing a plurality of fibers;
   irradiating the plurality of fibers with a high energy irradiation to generate an irradiated plurality of fibers;
   providing an aqueous solution comprising hydrophilic monomers;
   contacting the irradiated plurality of fibers with the aqueous solution such that the irradiated plurality of fibers is grafted with the hydrophilic monomers to provide a plurality of irradiated fibers having individual polymer chains extending from the surface thereof, wherein the individual polymer chains comprise hydrophilic groups; and
   removing residual hydrophilic monomers from the plurality of irradiated fibers.
Item 15. The method of item 14, wherein the high energy irradiation is at least one of e-beam irradiation or gamma irradiation.
Item 16. The method of item 14 or item 15, wherein the hydrophilic monomers comprise at least one unsaturated double bond.
Item 17. The method of any of items 14-16, wherein the hydrophilic monomers comprise a group that is either an acid or a base.
Item 18. The method of any of items 14-17, wherein removing the residual portion of hydrophilic monomers from the plurality of grafted fibers comprises washing the plurality of grafted fibers prior to reaction of the fibers with either an acid or a base.
Item 19. The method item 18, wherein washing comprises washing with water.
Item 20. The method of any of items 14-19, wherein the hydrophilic monomer comprises acrylic acid.

Item 21. The method of any of one of items 17-20, further comprising forming a salt of the group that is either an acid or base subsequent to removing residual hydrophilic monomers from the plurality of irradiated fibers.

Item 22. The method of any one of items 14-21, wherein irradiating the plurality of fibers with a high energy irradiation precedes contacting the plurality of fibers with the aqueous solution.

Item 23. The method of any one of items 14-21, wherein contacting the plurality of fibers with the aqueous solution occurs subsequent to irradiating the plurality of fibers with a high energy irradiation.

Item 24. The method of any one of items 14-23, wherein the aqueous solution further comprises a salt.

Item 25. The method of any one of items 14-24, wherein the plurality of fibers comprises cellulose-containing fiber.

Item 26. The method of any one of items 14-25, wherein the plurality of fibers comprises regenerated cellulose fiber.

Item 27. The method of any one of items 14-26, wherein removing the residual hydrophilic monomers leaves no more than 1 wt. % of the residual hydrophilic monomers in the plurality of irradiated fibers having grafted pendant hydrophilic groups.

Item 28. The method of any one of items 14-26, wherein removing the residual hydrophilic monomers leaves no more than 0.1 wt. % of the residual hydrophilic monomers in the plurality of irradiated fibers having grafted pendant hydrophilic groups.

Item 29. The method of any one of items 14-26, wherein removing the residual hydrophilic monomers leaves no more than 0.01 wt. % of the residual hydrophilic monomers in the plurality of irradiated fibers having grafted pendant hydrophilic groups.

Item 30. A method of making a hydrophilic nonwoven article, comprising:
 making a plurality of irradiated fibers having grafted pendant hydrophilic groups according to the method of any one of items 12 to 29; and
 forming a nonwoven article from the plurality of irradiated fibers having grafted pendant hydrophilic groups.

Item 31. A method of making a hydrophilic nonwoven article, comprising:
 making a first plurality of fibers having grafted pendant hydrophilic groups according to the method of any one of items 14 to 29;
 providing a second plurality of fibers not treated according to the method of item 14; and
 forming a nonwoven article from the first plurality of fibers and the second plurality of fibers.

Item 32. A method of making a hydrophilic nonwoven article, comprising:
 making a first plurality of fibers having grafted pendant hydrophilic groups according to the method of any one of items 14 to 29;
 making a second plurality of fibers having grafted pendant hydrophilic groups according to the method of any one of items 14 to 29; and
 forming a nonwoven article from the first plurality of fibers and the second plurality of fibers;
 wherein the first and second pluralities of fibers differ from each other in composition.

Item 33. A method of treating a wound, comprising:
 providing a hydrophilic nonwoven article according to any one of items 30 to 32; and
 contacting the hydrophilic nonwoven article onto a wound.

Item 34. A wound dressing article comprising a plurality of hydrophilic fibers made according to the method of any one of items 14-29.

Item 35. A wound dressing article comprising a hydrophilic nonwoven article made according to the method of any one of items 30 to 32.

Item 36. A wound dressing article, comprising a porous nonwoven material, the nonwoven material comprising porous fibers having grafted acrylic acid groups extending from the surfaces thereof.

Item 37. The wound dressing article of item 36, wherein grafted acrylic acid groups extend from the surfaces as non-crosslinked chains.

Item 38. The wound dressing article of item 36, wherein the nonwoven material has a fewer than 10% of bound nodes.

Item 39. The wound dressing article of item 36, wherein the porous fibers further comprise a grafted PEG material.

Item 40. The wound dressing article of item 36, wherein the porous fibers comprise a thermoplastic material.

Item 41. The wound dressing article of item 36, wherein the grafted acrylic acid groups extending from the surface form chains of 1 to 500 acrylic acid units.

Objects and advantages of the disclosure are further illustrated by the following examples, but the particular materials and amounts thereof recited in these examples, as well as other conditions and details, should not be construed to be unduly limiting. Unless otherwise indicated, all parts and percentages are on a weight basis, all water is distilled water, and all molecular weights are weight average molecular weight.

EXAMPLES

Materials utilized in the preparation of the examples are shown in Table 1.

TABLE 1

Component List

| Component | Source | Description |
|---|---|---|
| AMPS-ammonium salt | Lubrizol (Wickliffe, OH) | 2-acrylamido-2-methylpropane sulfonic acid (ammonium salt) monomer |
| SR550 | Sartomer (Exton, PA) | Methoxy polyethylene glycol monomethacrylate monomer |
| Acrylic acid (AA) | Sigma Aldrich (St. Louis, MO) | Acrylic acid monomer |
| LYOCELL TENCEL fibers | Lenzing AG (Mobile, AL) | 1.3 decitex × 38 mm regenerated cellulosic fibers |

Test Methods
Water Absorbency
 A sample of dried fibers were weighed (dry weight), then completely hydrated with distilled water. Excess water was decanted from the fibers. The wet fiber sample was then weighed (wet weight). A Water Absorbency Ratio was calculated according to the following equation:

Water Absorbency Ratio=wet weight/dry weight

Total Organic Carbon
 Total Organic Carbon determination was performed according to "Standard Method for the Examination of Water and Wastewater", Method 5310C.

Monomer Conversion Level
 The weight of the fiber used for the reaction was subtracted from the grafted fiber weight. The resulting value was divided by the weight of the monomer(s) used for the reaction. The resulting number was multiplied by 100 to provide a monomer conversion (%).

Electron beam (e-beam) irradiation was performed using an e-beam apparatus (available from Energy Sciences Inc., Wilmington, Mass., under the trade designation "MODEL CB-300 ELECTRON BEAM SYSTEM") to deliver electron beam irradiation at the dosage level indicated in each Example.

Example 1

LYOCELL TENCEL fibers (8 g) were heat sealed in a plastic bag under a nitrogen atmosphere. The fibers were subjected to electron beam irradiation resulting in a 60 kGy total dose. The fibers were added to a monomer solution that had been equilibrated in nitrogen gas environment containing 4 g AMPS-ammonium salt ($1.78 \times 10^{-2}$ mol) and 15 g sodium chloride in 100 g water ($2.23 \times 10^{-3}$ mol monomer/g fiber). The fibers were reacted in a nitrogen atmosphere for 18 hrs, washed with water, then by vacuum filtered. The resulting monomer-grafted fibers were dried at 55° C. and weighed. A final weight of 8.8 g was obtained, resulting in 20% monomer conversion.

Examples 2-3

A similar procedure was used as described in Example 1, but with different monomers. Details are shown in Table 2.

TABLE 2

Preparation of Examples 1-3

| Example | Monomer | Final Weight (g) | Monomer Conversion (%) |
|---|---|---|---|
| 1 | 4 g AMPS-ammonium salt | 8.8 | 20 |
| 2 | 4 g SR550 | 11.8 | 95 |
| 3 | 3 g SR550<br>1 g AMPS-ammonium salt | 11.3 | 83 |

Example 4

LYOCELL TENCEL fibers (8 g) were heat sealed in a plastic bag under a nitrogen atmosphere. The fibers were subjected to electron beam irradiation resulting in a 70 kGy dose. The fibers were added to a monomer solution that had been equilibrated in nitrogen gas environment containing 7 g AA ($9.72 \times 10^{-2}$ mol) and 3 g SR550 ($7.58 \times 10^{-3}$ mol) in 100 g water ($1.31 \times 10^{-3}$ mol monomers/g fiber). The fibers were reacted in a nitrogen atmosphere for 18 hrs, and then were suspended in 250 ml water. Sodium hydroxide (50% w/w, 7.8 mL) was added to the fiber suspension to convert the AA to the sodium salt. The fiber suspension was stirred for 1 hr and the fibers were filtered under vacuum. The resulting fibers were washed with water and vacuum filtered. The resulting monomer-grafted fibers were dried at 55° C. and weighed. A final weight of 19.4 g was obtained, resulting in 96% monomer conversion.

Examples 5-7

A similar procedure was used as described in Example 4, but with different monomers. Details are shown in Table 3.

TABLE 3

Preparation of Examples 4-7

| Example | Monomer | Final Weight (g) | Monomer Conversion (%) |
|---|---|---|---|
| 4 | 7 g AA<br>3 g SR550 | 19.4 | 92 |
| 5 | 10 g AA<br>5 g SR550 | 24.7 | 90 |
| 6 | 12 g AA<br>5 g SR550 | 26.3 | 88 |
| 7[a] | 15 g AA<br>7 g SR550 | 32.7 | 93 |

[a]cross-linking appeared to occur during the reaction

Example 8

LYOCELL TENCEL fibers (150 g, 1.7 decitex ("dtex"), 51 mm) were packed in a FOODSAVER plastic bag and vacuum sealed under a nitrogen atmosphere. The bag was placed in an insulated shipping box containing dry ice. The box was irradiated with gamma-irradiation using a Cobalt-60 source for a total dose of approximately 62 kGy. The resulting fibers were removed from the bag under a nitrogen atmosphere and added to a monomer solution consisting of 2,194 g distilled water, 158 g AA, and 48 g SR550 that had been degassed with nitrogen. The fibers were reacted with the monomer solution for 18 hrs under a nitrogen gas atmosphere. Two purification methods were assessed.

Purification Method 1:

Radiation grafted fibers (50 g) were hydrated with 20 ml distilled water and squeezed to remove liquid from the fibers. This process was repeated 10 times (200 ml total volume of water). The fibers were then added to 200 ml distilled water containing 3.4 g of 50% sodium hydroxide. The fibers were stirred for 2 minutes and filtered under vacuum using a fitted filter. The fibers were washed with 200 ml distilled water to remove any residual sodium hydroxide. A final wash using 200 ml distilled water was conducted and the resulting filtrate was collected. Sulfuric acid (3 ml) was added to stabilize the solution for Total Organic Carbon analysis.

Purification Method 2:

Radiation grafted fibers (50 g) were added to 200 ml distilled water containing 3.4 g of 50% sodium hydroxide. The fibers were stirred for 2 minutes and filtered under vacuum using a fritted filter. The fibers were washed with 200 ml distilled water (×4, 800 ml total) to remove any residual sodium hydroxide. A final wash using 200 ml distilled water was conducted and the resulting filtrate was collected. Sulfuric acid (3 ml) was added to stabilize the solution for Total Organic Carbon analysis.

Total Organic Carbon was measured using the method SM 5310C with a reporting limit of 1 mg/ml. The filtrate from method 1 contained no detectable total organic carbon, which the filtrate from method 2 contained 2.6 mg/ml total organic carbon.

Examples 9-12

LYOCELL TENCEL fibers (6 g, 1.7 dtex, 51 mm) were packed in four separate FOODSAVER plastic bags and vacuum sealed under a nitrogen atmosphere. The bags were irradiated using e-beam at a dose of 50 kGy. The resulting fibers were removed from the bags under a nitrogen atmosphere and added to four separate monomer solutions. The fibers were reacted in a nitrogen atmosphere for 18 hrs, and then were suspended in 250 ml water. Sodium hydroxide was added to the fiber suspension to convert the AA to the sodium salt. The moles of monomer (AA plus SR550) grafted and the Water Absorbency levels were measured. Compositions and data are shown in Table 4.

Examples 13-15

Examples 13-15 were prepared in a similar manner to Examples 9-12 with the exception that the fibers were 3.3 dtex and 60-90 mm in length. Compositions and data are shown in Table 4.

TABLE 4

Water Absorbency vs. Monomer Graft

| Example | Monomer | Final Weight (g) | Monomers/ Fiber (mol/g) | Water Absorbency (%) |
|---|---|---|---|---|
| 9 | 3.14 g AA 0.55 g SR550 | 10.3 | 0.0075 | 15.9 |
| 10 | 4.17 g AA 0.73 g SR550 | 12.0 | 0.0100 | 20.3 |
| 11 | 5.22 g AA 0.92 g SR550 | 13.7 | 0.0125 | 24.9 |
| 12 | 6.29 g AA 1.23 g SR550 | 15.1 | 0.0150 | 27.7 |
| 13 | 4.17 g AA 0.73 g SR550 | 9.5 | 0.0100 | 15.5 |
| 14 | 5.22 g AA 0.92 g SR550 | 11.1 | 0.0125 | 16.8 |
| 15 | 6.29 g AA 1.23 g SR550 | 12.5 | 0.0150 | 21.2 |

Example 16

LYOCELL TENCEL fibers (6 g, 3.3 dtex, 60-90 mm) were packed in eight separate FOODSAVER plastic bags and vacuum sealed under a nitrogen atmosphere. The bags were irradiated using an e-beam at a dose of 50 kGy. The resulting fibers were removed from the bags under a nitrogen atmosphere and added to ten individual containers containing a monomer solution of 88.68 g distilled water, 6.29 g AA, and 1.23 g SR550 that had been degassed with nitrogen. Irradiated fibers (6 g) were reacted with the monomer solution under a nitrogen gas atmosphere for a specific time, and then were tested for weight gain. Results are shown in Table 5.

TABLE 5

Weight Gain vs. Time

| Reaction Time (hours) | Weight Gain (g) |
|---|---|
| 0.5 | 6.08 |
| 1.0 | 6.08 |
| 2.0 | 6.30 |
| 3.0 | 6.24 |
| 4.0 | 6.21 |
| 8.0 | 6.28 |
| 10.0 | 7.17 |
| 18.0 | 6.39 |

Examples 17-22

Tencel fibers (6 g, 1.7 dtex, 51 mm) were packed in six separate FOODSAVER plastic bags and vacuum sealed under a nitrogen atmosphere. Three bags were irradiated using an e-beam at a dose of 50 kGy (Examples 17-19) and three bags were irradiated using an e-beam at a dose of 100 kGy (Examples 20-22). The resulting fibers were removed from the bags under a nitrogen atmosphere, and added to a monomer solution, and reacted for 18 hours. The grafted fibers were washed to remove unreacted monomers. The fibers were further processed to provide the sodium salt of the acid group. Fibers were added to 500 ml distilled water containing 7.0 g of 50% sodium hydroxide. The fibers were stirred for 5 minutes and filtered under vacuum using a fitted filter. The fibers were washed with 200 ml distilled water to remove residual sodium hydroxide. A final wash was conducted using 500 ml distilled water and the fibers were collected by filtration. Compositions and test data are shown in Table 6.

TABLE 6

Water Absorbency vs. Monomer Graft

| Example | Monomer | Final Weight (g) | Molecules AA/Molecules Glucose |
|---|---|---|---|
| 17 | 4.17 g AA 0.73 g SR550 | 10.4 | 1.16 |
| 18 | 5.22 g AA 0.92 g SR550 | 12.4 | 1.50 |
| 19 | 6.29 g AA 1.23 g SR550 | 13.6 | 1.96 |
| 20 | 4.17 g AA 0.73 g SR550 | 10.8 | 1.26 |
| 21 | 5.22 g AA 0.92 g SR550 | 12.2 | 1.65 |
| 22 | 6.29 g AA 1.23 g SR550 | 14.0 | 2.30 |

What is claimed is:

1. A wound dressing comprising:
   a nonwoven web comprising a plurality of fibers irradiation-grafted with individual polymer chains that extend from the surface of the fibers;
   wherein the individual polymer chains comprise monomers having at least one poly(alkylene oxide) group and anionic monomers having at least one hydrophilic group;
   wherein the monomers having at least one poly(alkylene oxide) group make up 2 to 25 wt. % of all monomers making up the polymer chains; and
   wherein the polymer chains are not cross-linked to any appreciable extent.

2. The wound dressing of claim 1, wherein the nonwoven web has a specific density of no more than 0.1 gram per cubic centimeter.

3. The wound dressing of claim 1, wherein the plurality of fibers comprise cellulose.

4. The wound dressing of claim 1, wherein the individual polymer chains comprise acrylic acid monomer units.

5. The wound dressing of claim 4, wherein the individual polymer chains further comprise polyethylene glycol monomer units.

6. The wound dressing of claim 1, wherein the hydrophilic groups comprise carboxylic acid groups or a salt thereof, or a combination of carboxylic acid groups and a salt thereof.

7. The wound dressing of claim 6, wherein the salt comprises metal ions, wherein the metal ions comprise any of sodium ions, potassium ions, rubidium ions, zinc ions, calcium ions, or combinations thereof.

8. The wound dressing of claim 1, wherein the Water Absorbency Ratio is at least 15.

9. The wound dressing of claim 1, wherein the Water Absorbency Ratio is at least 20.

10. The wound dressing of claim 1, further comprising at least one of an antibacterial agent, an anti-inflammatory agent, an anesthetic agent, an anti-odor agent, or combinations thereof.

11. The wound dressing of claim 1, wherein at least a portion of the nonwoven web absorbs wound fluid.

12. The wound dressing of claim 1, wherein fibers in the plurality of fibers comprise fiber repeat units, and wherein the nonwoven web has a ratio of hydrophilic groups to fiber repeat units in a range of from 1 to 3.

13. The wound dressing of claim 1, wherein fibers in the plurality of fibers comprise fiber repeat units, and wherein the nonwoven web has a ratio of hydrophilic groups to fiber repeat units in a range of from 0.25 to 5.0.

* * * * *

UNITED STATES PATENT AND TRADEMARK OFFICE
CERTIFICATE OF CORRECTION

PATENT NO. : 9,907,702 B2
APPLICATION NO. : 14/237205
DATED : March 6, 2018
INVENTOR(S) : Cary Kipke It is certified that error appears in the above-identified patent and that said Letters Patent is hereby corrected as shown below:

In the Specification

Column 1
Line 8 (Approx.)   Delete "PCT/US2012/0505018," and insert -- PCT/US2012/050518, --, therefor.

Column 5
Line 6   Delete "2-isocyanatoethyl(meth)acrylate." and insert -- 2-isocyanatoethyl (meth)acrylate. --, therefor.
Line 26  Delete "Shinnakamura" and insert -- Shin-Nakamura --, therefor.

Column 16
Line 38   Delete "fitted" and insert -- fritted --, therefor.

Column 18
Line 11   Delete "fitted" and insert -- fritted --, therefor.

Signed and Sealed this
Twenty-second Day of May, 2018

Andrei Iancu
*Director of the United States Patent and Trademark Office*